United States Patent
Mahfouz (10) Patent No.: US 10,213,128 B2
(45) Date of Patent: Feb. 26, 2019

(54) UWB MICROWAVE IMAGING SYSTEM WITH A NOVEL CALIBRATION APPROACH FOR BREAST CANCER DETECTION

(71) Applicant: Joint Vue, LLC, Knoxville, TN (US)

(72) Inventor: Mohamed R. Mahfouz, Knoxville, TN (US)

(73) Assignee: JointVue LLC, Knoxville, TN (US)

( * ) Notice: Subject to any disclaimer, the term of this patent is extended or adjusted under 35 U.S.C. 154(b) by 0 days.

(21) Appl. No.: 15/640,849

(22) Filed: Jul. 3, 2017

(65) Prior Publication Data

US 2017/0296091 A1    Oct. 19, 2017

Related U.S. Application Data

(60) Division of application No. 13/857,608, filed on Apr. 5, 2013, now abandoned, which is a continuation of application No. PCT/US2011/054952, filed on Oct. 5, 2011.

(60) Provisional application No. 61/389,863, filed on Oct. 5, 2010.

(51) Int. Cl.
*A61B 5/00* (2006.01)
*A61B 5/05* (2006.01)

(52) U.S. Cl.
CPC ............ *A61B 5/0507* (2013.01); *A61B 5/708* (2013.01)

(58) Field of Classification Search
CPC .............................. A61B 5/0507; A61B 5/708
See application file for complete search history.

(56) References Cited

U.S. PATENT DOCUMENTS

| | | | |
|---|---|---|---|
| 6,061,589 A * | 5/2000 | Bridges | A61B 5/05 600/430 |
| 7,454,242 B2 | 11/2008 | Fear et al. | |
| 7,570,063 B2 | 8/2009 | Van Veen et al. | |
| 2004/0077943 A1 | 4/2004 | Meaney et al. | |
| 2005/0107693 A1 | 5/2005 | Fear et al. | |
| 2007/0016006 A1 | 1/2007 | Shachar | |
| 2007/0282200 A1 | 12/2007 | Johnson et al. | |
| 2009/0015832 A1 | 1/2009 | Popovic et al. | |
| 2009/0129652 A1 | 5/2009 | Zwirn et al. | |
| 2011/0137149 A1 * | 6/2011 | Gertner | A61B 5/412 600/411 |
| 2011/0237939 A1 * | 9/2011 | Melamed | A61B 8/08 600/425 |

FOREIGN PATENT DOCUMENTS

| | | |
|---|---|---|
| EP | 11831535 | 8/2014 |
| WO | 2007105963 | 9/2007 |
| WO | 2012048020 | 1/2012 |
| WO | 2012048020 | 4/2012 |
| WO | 2012048020 | 4/2013 |

* cited by examiner

*Primary Examiner* — Joel Lamprecht
(74) *Attorney, Agent, or Firm* — Dorton & Willis LLP; Ryan Willis (57) ABSTRACT

An apparatus and method for imaging a tissue. The method includes transmitting a first microwave frequency signal to and receiving a first total signal from the tissue at a first position. A second microwave frequency signal is transmitted to and a second total signal received from the tissue at a second position. The first total signal is calibrated with respect to the second total signal and an image is constructed from the calibrated signal.

13 Claims, 9 Drawing Sheets

UWB MICROWAVE IMAGING SYSTEM WITH A NOVEL CALIBRATION APPROACH FOR BREAST CANCER DETECTION

This application is a divisional of U.S. patent application Ser. No. 13/857,608, filed Apr. 5, 2013 and titled, "UWB Microwave Imaging System with A Novel Calibration Approach For Breast Cancer Detection," which is a continuation of International PCT Application No. PCT/US2011/054952, filed Oct. 5, 2011, entitled "UWB MICROWAVE IMAGING SYSTEM WITH A NOVEL CALIBRATION APPROACH FOR BREAST CANCER DETECTION", which claims the benefit of U.S. Provisional Application No. 61/389,863, filed Oct. 5, 2010, entitled "UWB MICROWAVE IMAGING SYSTEM WITH A NOVEL CALIBRATION APPROACH FOR BREAST CANCER DETECTION", the disclosures of which applications are hereby incorporated by reference herein in their entireties.

FIELD OF THE INVENTION

The present invention relates generally to medical imaging modalities and, more particularly, to a microwave imaging system.

BACKGROUND OF INVENTION

Microwave imaging technology is attractive as an alternative solution for tumor detection, and particularly, for breast cancer detection. Microwave imaging technology is lower-cost and shorter operation time as compared to magnetic resonance imaging ("MRI") and is less invasive than X-ray.

However, a problem associated with microwave imaging is the low contrast condition for the detection of a malignant tumor. Recent studies have indicated that nearly all breast cancers originate in the glandular tissues of the breast. The dielectric property differences between malignant tissues and glandular tissue is generally not more than 10%. With this slight difference in dielectric properties, the expected reflected/scattered signal from the malignant tumor is very weak. One the other hand, the received signals due to skin backscatter and coupling of the transmitting and receiving antenna ("Tx" and "Rx," respectively) are comparatively much stronger. Therefore, the desired signal from the tumor is typically immersed in various noise signals.

Conventional methods for overcoming the desired signal to noise ratio have included various calibration and contrast agents. In calibrating the signal, generally the signal acquired from a known, non-tumor region of the breast tissue is subtracted from the signal acquired from the tumor containing region. While this method has been useful in eliminating noise, the method is not practical for real clinical diagnosis since the reference signal is not generally available. Contrast agents, such as golden nano-particles or carbon nano-tubes have been considered; however, some patients may not accept any agent injections.

Therefore, there continues to be a need for signal processing methods that improve the sensitivity of tumor detection by microwave imaging technologies.

SUMMARY OF THE INVENTION

The present invention overcomes the foregoing problems and other shortcomings, drawbacks, and challenges of the conventional microwave imaging technology by presenting a diagnostic imaging device and method that uses microwave imaging for identify a target, such as a tissue mass or tumor, by calibrating an acquired microwave signal prior to image construction. While the invention will be described in connection with certain embodiments, it will be understood that the invention is not limited to these embodiments. To the contrary, this invention includes all alternatives, modifications, and equivalents as may be included within the spirit and scope of the present invention.

In accordance with one embodiment of the present invention, a method for imaging a tissue includes transmitting a first microwave frequency signal to and receiving a first total signal from the tissue at a first position. A second microwave frequency signal is transmitted to and a second total signal received from the tissue at a second position. The first total signal is calibrated with respect to the second total signal and an image is constructed from the calibrated signal.

According to another embodiment of the present invention, a medical imaging device includes a tissue support having a size and shape to receive a tissue. At least one transducer is operably coupled to the tissue support. The at least one transducer includes a transmitting antenna operable in a frequency range of about 2 GHz to about 8 GHz and a receiving antenna operable in a frequency range of about 2 GHz to about 8 GHz. The at least one transducer transmits a first signal and receives a first total signal at a first position with respect to the tissue and transmits a second signal and receives a second total signal at a second position with respect to the tissue.

Still, in accordance with another embodiment of the present invention, a medical imaging device includes a tissue support having a size and shape to receive a tissue. A plurality of transducers is coupled to the tissue support. Each of the plurality of transducers includes a transmitting antenna operable in a frequency range of about 2 GHz to about 8 GHz and a receiving antenna operable in a frequency range of about 2 GHz to about 8 GHz. A select one of the plurality of transducers transmits a first signal and receives a first total signal at a first position and an adjacent one of the plurality of transducers transmits a second signal and receives a second total signal at a second position.

One embodiment of the present invention is directed to a method of reconstructing an imaging of a tissue from first and second microwave signals and includes receiving the first and second microwave signals as reflected from the tissue at respective first and second positions. The first microwave signal is calibrated with the second microwave signal and the image is constructed form the calibrated signal.

Another embodiment of the present invention is directed to a method of scanning a tissue and includes transmitting a first microwave frequency signal to the tissue at a first position. A first total signal reflected from the tissue at the first is received. A second microwave frequency signal is transmitted to the tissue at a second position, and a second total signal reflected from the tissue at the first is received. The first and second positions are separated by less than about 20 mm.

The above and other objects and advantages of the present invention shall be made apparent from the accompanying drawings and the descriptions thereof.

BRIEF DESCRIPTION OF THE FIGURES

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Turning now to the figures, an imaging system in accordance with various embodiments of the present invention is described. The imaging system may include a tissue cup, for example, an imaging cup, in the shape of the tissue being imaged. The imaging cup, such as for use in imaging breast tissue, may be rigid, may include a disposable polymeric hygienic liner, and may include at least one microwave antenna. The liner may be polyurethane or silicone gel, such as those that are commercially-available from Ohio Willow Wood (Mt. Sterling, OH). The liner increases patient comfort, reduces air bubbles at the skin interface, minimizes skin slippage, and may decrease the dielectric impedance mismatch for optimal signal propagation. It is readily understood by those skill in the art that additional electronics are incorporated via wire or traces to access, drive, and/or process the microwave antenna and the signals transmitted and/or received by the same.

The sending and receiving of microwave signals may be achieved by various types and designs of antennae, the size of which is largely governed by the dielectric constant, er, of the fabrication materials. One such example is a patch antenna. Dielectric resonators or any other microwave device may also be used for signal transmission and reception. These microwave antennae or resonators may be positioned, or arrayed, within the imaging cup. Various sizes of imaging cups may be required for appropriately fitting the particular anatomy of the patient to ensure skin contact with the antennae or resonators. Thus, the number of antennae or microwave devices required is related to the surface density, wherein a larger number of antennae is required for a breast having a larger surface area. The rigidity of the cup reduces, or eliminates, movement between the individual microwave devices.

Some embodiments may include a cup assembly that seals the antenna(e) into a conformable polymeric material. The polymeric material may be the same described above and may be used with a hygienic liner. The polymeric material may reduce or eliminate the need for gels or other impedance matching material.

Figure 1:
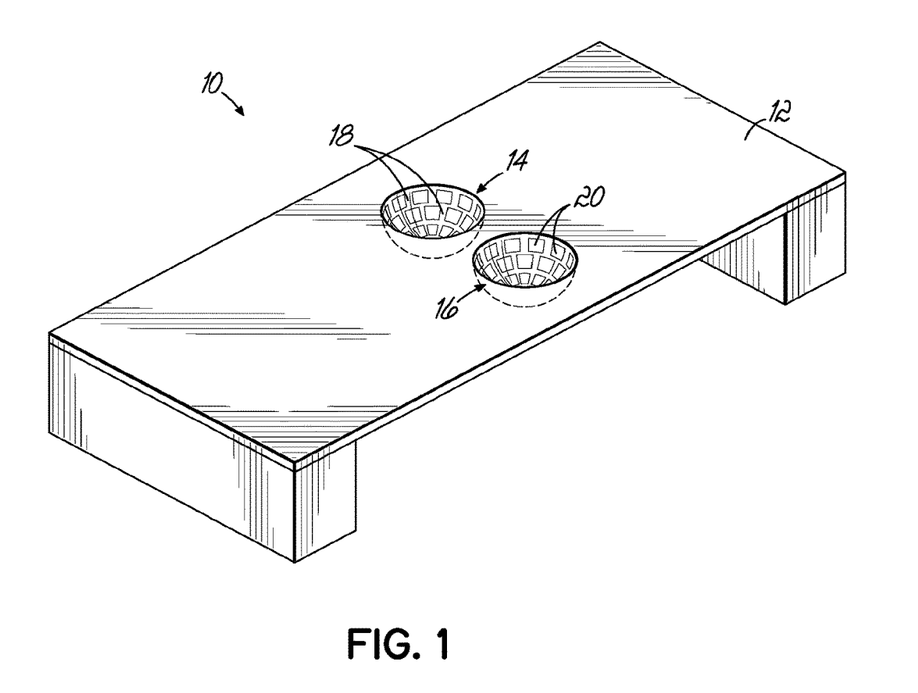
FIG. 1 is a perspective view of a microwave imaging system having two imaging cups for detection of breast cancer in accordance with one embodiment of the present invention.

With reference now in particular to FIG. 1, a microwave imaging system ("imaging system" 10) for use in detecting breast cancer in accordance with one embodiment of the present invention is described. The imaging system 10 includes a planar support 12 with first and second tissue supports 14, 16 therein, wherein the tissue supports are specifically illustrated as breast imaging cups. The imaging system 10 may be arranged such that the patient (not shown) may lie upon the planar support 12 with the left breast (not shown) in a first imaging cup 14 and the right breast (not shown) in the second imaging cup 16.

It will be readily appreciated that while the features of the present invention are described with reference to breast imaging, the various features may be altered, as would be known to those of ordinary skill in the art, for imaging other portions of a patient's anatomy. Furthermore, while the planar support 12 is schematically illustrated as a basic support, it would be readily understood that the first and second imaging cups 14, 16 may alternatively be positioned in an examination table or a rotatable table that may be rotated to an upright position so that the patient, with the table, may together be rotated into the supine position.

In still other embodiments, the first and second imaging cups 14, 16 may be formed separate from any planar support and positioned directly onto the breasts. Moreover, only one imaging cup may be used, with one breast imaged first and then the other breast imaged subsequently. Moreover, and as described in greater detail below, the imaging cups may also be formed separately and incorporated into a supportive brassiere 17 for the patient to wear during imaging, allowing a more comfortable stance for the patient.

In the particular illustrated embodiment, the first and second imaging cups 14, 16 may have a shape that is conical, hemispherical, paraboloidal, or other as appropriate to receive the patient's breast.

Each imaging cup 14, 16 includes a plurality of transducers 18, 20, each transducer 18, 20 being located at a position, $P^i$, along the surface of the imaging cup 14, 16. Any number of transducers 18, 20 may be used and may be arranged, as shown, in one or more rows with each adjacent transducer being separated by a small distance (in Cartesian coordinates) or small angle (in polar coordinates), for example, about 1 degree, about the circumference of the imaging cup 14, 16. As described in greater detail below, other arrangements may also be used, and the arrangements of the imaging cups should not limited to the particular shape and number of transducers shown.

Figure 2:
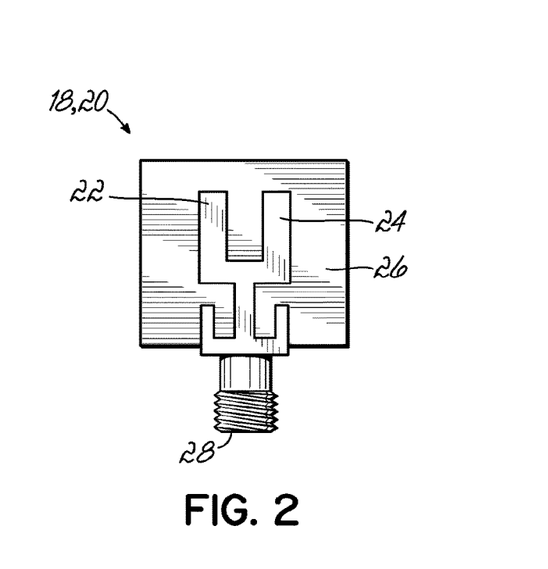
FIG. 2 is a side elevational view of an imaging transducer in accordance with one embodiment of the invention.

Turning now to FIG. 2, one transducer is shown in greater detail. The transducer 18, 20 includes transmitting and receiving antenna 22, 24 ("Tx" and "Rx," respectively) for transmitting a first electromagnetic signal and receiving a second electromagnetic signal in accordance with the general concepts of microwave imaging technologies. As is well known by those of ordinary skill in the art, a single antenna may also act as a whole, and may be used for both the transmitting and receiving functions, alternatively eliminating the need for the separate Tx and Rx antennae 22, 24. The single antenna may also be used for Tx and Rx at a single point in time and switched to the opposite mode when needed. The Tx and Rx antennae 22, 24 may be fabricated on a substrate 26, which, for example, may include a 31-mil thick Rogers RT5880 substrate (Rogers Corp. Rogers, CT) having a dielectric constant, k, of about 2.2 and a loss tangent of about 0.0009. An adaptor 28 may be configured to electrically-couple the transducer 18, 20 to the various other electrical components of the imaging system 10 (FIG. 1). In would be readily appreciated that other fabrication tools and methods may also be used, as is known to those of ordinary skill in the art.

Generally, the Tx antenna 22 transmits the electromagnetic signal, operating, for example, in the frequency range of about 2 GHz to about 8 GHz. The transmitted first signal is scattered and/or reflected at various interfaces of varying dielectric characteristics, which may include the tissue-air interface and the interface between the glandular tissue of the breast and the malignant tumor tissue, e.g., a target, therein. The Rx antenna 24 receives the various reflected and/or scattered second signals, which may include signals as a result of signal coupling of the Tx and Rx antennae 22, 24, backscatter from the tissue-air interface, reflections from the target, miscellaneous reflections, and other signals as are known to those of ordinary skill in the art. The Rx antenna 24 operates, for example, in the frequency range of about 2 GHz to about 8 GHz.

Figure 3:
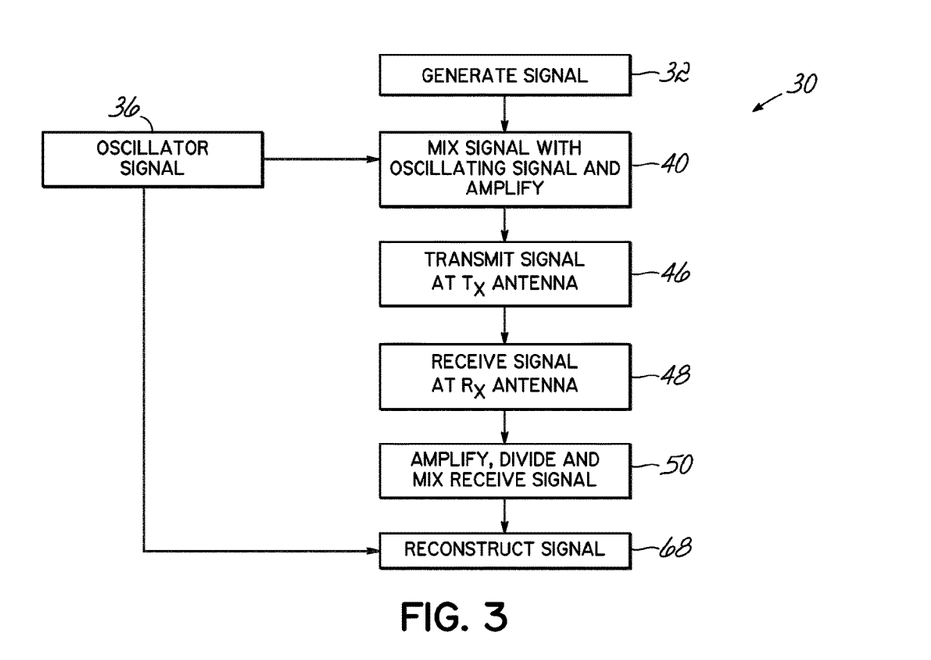
FIG. 3 is a flow chart illustrating one method of transmitting and acquiring a microwave signal in accordance with one embodiment of the invention.
Figure 4:
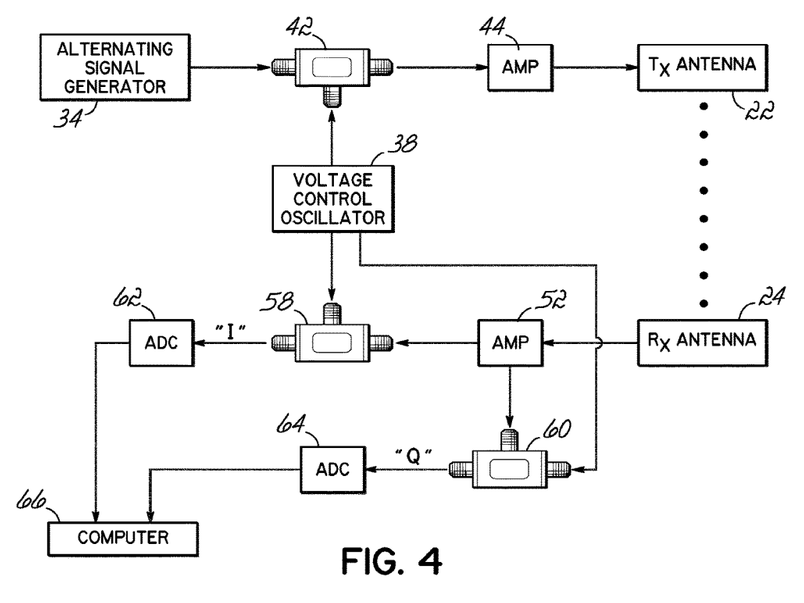
FIG. 4 is a schematic electrical diagram of the imaging system in accordance with one embodiment of the present invention.

With reference to FIGS. 3 and 4, as well as continued reference to FIG. 2, the electronic arrangement and a method 30 of generating the transmitted signal, transmitting the signal, receiving the scattered/reflected signal, and preparing the received signal are shown and described in greater detail.

Operation of the transducer 18, 20 begins with generating a signal (Block 32) at an alternating signal generator 34. More specifically, signal generation may include a driving clock that is used to drive a pulse generator. In some embodiments, an FPGA circuit may be used to generate the driving clock, which drives a 300 ps Gaussian pulse generator. The alternating signal may then be mixed with an oscillating signal 36, such as input from a voltage control oscillator 38, and amplified (Block 40). Mixing of the signal may occur in a signal mixer 42, such as a MITEQ DM0208 mixer (MITEQ Inc., Hauppauge, N.Y.), and amplified by a high-gain amplifier 44, such as a Mini-Circuits ZVE-8G+ Power Amplifier (Mini-Circuits, Brooklyn, N.Y.). The amplified signal is then transmitted to a wideband transmitter link of the transducer 18, 20 and transmitted by the Tx antenna 22 (Block 46). The Tx antenna 22 operates at 2-8 GHz to balance the competing requirements for imaging resolution and penetration depth into the breast tissue.

The signal is received by the Rx antenna 24 of the transducer 18, 20 (Block 48) and amplified, divided, and mixed (Block 50). In that regard, the received signal is amplified through a wideband low noise amplifier 52, such as the commercially-available Hittite HMC753 (Hittite Microwave Corp., Chelmsford, Mass.) and down-converted into an in-phase channel (illustrated as "I") and a quadrature-phase channel (illustrated as "Q"). The I and Q channel signals I, Q are each mixed at first and second mixers 58, 60, respectively, with the oscillating signal 36 that was generated by the voltage control oscillator 38. Each signal may then be low-pass filtered and converted at a respective analog-to-digital converter ("ADC" 62, 64). One suitable ADC 62, 64 may include the commercially-available MAX104 (Maxim Integrated Products, Inc., Sunnyvale, Calif.). Once converted to digital form, all collected signals may be stored, for example, in a field-programmable gate array ("FPGA"), such as the commercially-available Xilinx Vertex-4 FPGA evaluation board (Xilinx, Inc., San Jose, Calif.). Alternatively, or additionally, the signals may be transferred to a computer 66, such as by a USB2.0 (not shown) or wirelessly-transmitted using BLUETOOTH (Bluetooth Special Interest Group, Kirkland, Wash.) or any other robust data transfer protocol as is well known in the art, where the signal may be reconstructed (Block 68).

Figure 5:
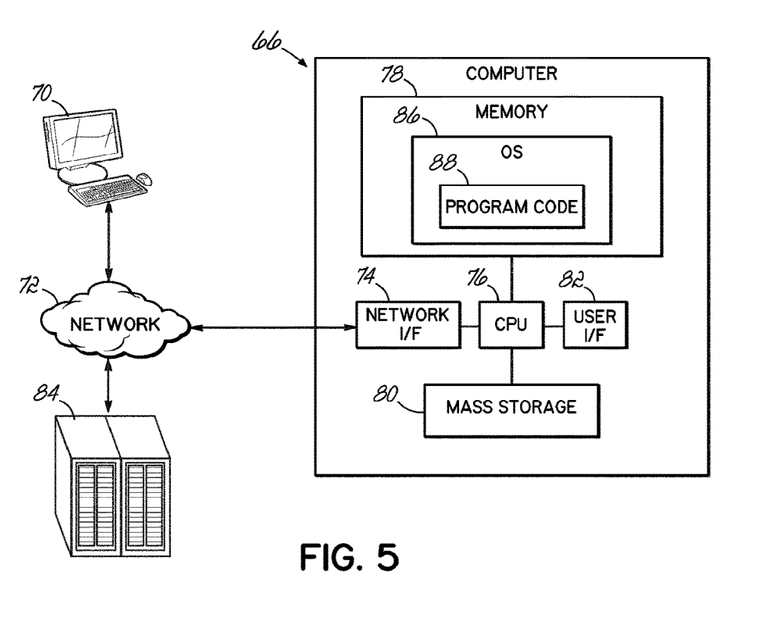
FIG. 5 is a diagrammatic view of a computer system suitable for use with the microwave imaging system in accordance with one embodiment of the present invention.

With reference to FIG. 5, the details of the computer 66 for operating the transducers 18, 20 (FIG. 2) and/or reconstructing the images from the acquired microwave signals is described. The computer 66 that is shown in FIG. 5 may be considered to represent any type of computer, computer system, computing system, server, disk array, or programmable device such as multi-user computers, single-user computers, handheld devices, networked devices, or embedded devices, etc. The computer 66 may be implemented with one or more networked computers 70 using one or more networks 72, e.g., in a cluster or other distributed computing system through a network interface (illustrated as "NETWORK I/F" 74). The computer 66 will be referred to as "computer" for brevity's sake, although it should be appreciated that the term "computing system" may also include other suitable programmable electronic devices consistent with embodiments of the present invention.

The computer 66 typically includes at least one processing unit (illustrated as "CPU" 76) coupled to a memory 78 along with several different types of peripheral devices, e.g., a mass storage device 80 with one or more databases (not shown), an input/output interface (illustrated as "USER I/F" 82), and the Network I/F 74. The memory 78 may include dynamic random access memory ("DRAM"), static random access memory (SRAM"), non-volatile random access memory ("NVRAM"), persistent memory, flash memory, at least one hard disk drive, and/or another digital storage medium. The mass storage device 80 typically includes at least one hard disk drive, and may be located externally to the computer 66, such as in a separate enclosure or in one or more of the networked computers 70, one or more networked storage devices 84 (including, for example, a tape or optical drive), and/or one or more other networked devices (including, for example, a server).

The CPU 76 may be, in various embodiments, a single-thread, multi-threaded, multi-core, and/or multi-element processing unit (not shown) as is well known in the art. In alternative embodiments, the computer 66 may include a plurality of processing units that may include single-thread processing units, multi-threaded processing units, multi-core processing units, multi-element processing units, and/or combinations thereof as is well known in the art. Similarly, the memory 78 may include one or more levels of data, instruction, and/or combination caches, with caches serving the individual processing unit or multiple processing units (not shown) as is well known in the art.

The memory 78 of the computer 66 may include one or more applications (illustrated as "PROGRAM CODE" 88), or other software program, which are configured to execute in combination with an operating system (illustrated as "OS" 86) and automatically perform tasks necessary for operating the transducers 18, 20 (FIG. 2) and/or reconstructing the images with or without accessing further information or data from the database(s) of the mass storage device 80.

Those skilled in the art will recognize that the environment illustrated in FIG. 5 is not intended to limit the present invention. Indeed, those skilled in the art will recognize that other alternative hardware and/or software environments may be used without departing from the scope of the invention.

Figure 6:
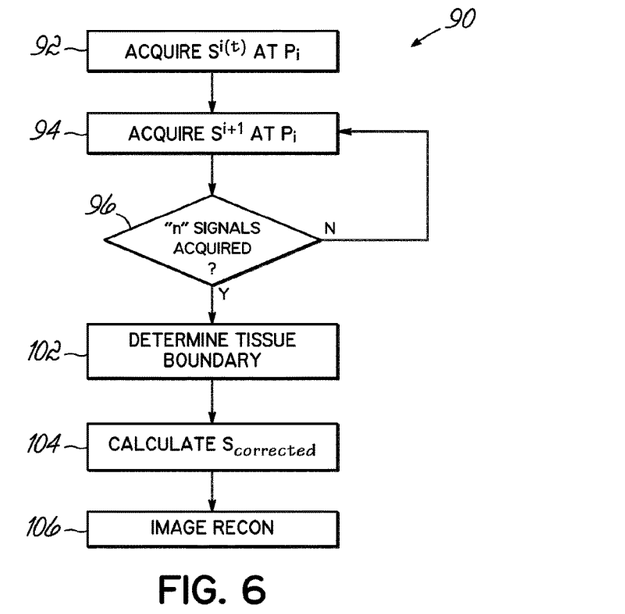
FIG. 6 is a flow chart illustrating one method of processing the acquired signal in accordance with one embodiment of the present invention.

In use, and with reference now to FIG. 6, a method 90 of reconstructing an image from the acquired signals is described. A first transducer 18, 20 (FIG. 1) associated with either or both of the first and second imaging cups 14, 16 (FIG. 1) and located at a first position, $P_i$, is operated and a signal received, $S^i(t)$ (Block 92), wherein the total signal is given by:

$$S^i(t) = S_{coupling}^i(t) + S_{skin}^i(t) + S_{target}^i(t) + S_{mr}^i(t)$$

where $S_{coupling}^i(t)$ is the portion of the signal due to the mutual coupling between the Tx antenna and the Rx antenna, $S_{skin}^i(t)$ is the portion of the signal due to backscatter at the air/skin interface, $S_{target}^i(t)$ is the portion of the signal due to the reflection/scattering from the target, i.e., the tumor, and $S_{mr}^i(t)$ is the portion of the signal due to multi-reflections.

Sequentially, or simultaneously, a transducer 18, 20 (FIG. 1) associated with either or both of the first and second imaging cups 14, 16 (FIG. 1) and located at a second position, $P_{i+1}$, is operated and a signal received, $S^{i+1}(t)$, (Block 94) wherein the total signal is given by:

$$S^{i+1}(t) = S_{coupling}^{i+1}(t) + S_{skin}^{i+1}(t) + S_{target}^{i+1}(t) + S_{mr}^{i+1}(t)$$

After the signal at the second position is acquired, a determination is made as to whether "n" signals have been acquired (Block 96). That is, if the first imaging cup 14 (FIG. 1) includes 50 transducers 18 (FIG. 1), then signals from each of the 50 transducers 18 (FIG. 1) should be acquired and n would equal 50. Alternatively, if a single transducer 98 (FIG. 11) is used, such as is illustrated and described below with reference to FIG. 11, then a discrete number of positions of the single transducer 98 (FIG. 11) along the track 100 should be acquired. For example, if the position of the single transducer 98 (FIG. 11) is move by 1 degree for each position, then n would equal 360.

If n signals have not been acquired ("NO" branch of Decision Block 96), then the method 90 returns to further acquire a signal at another position (Block 94). Otherwise, the process continues.

Figure 7:
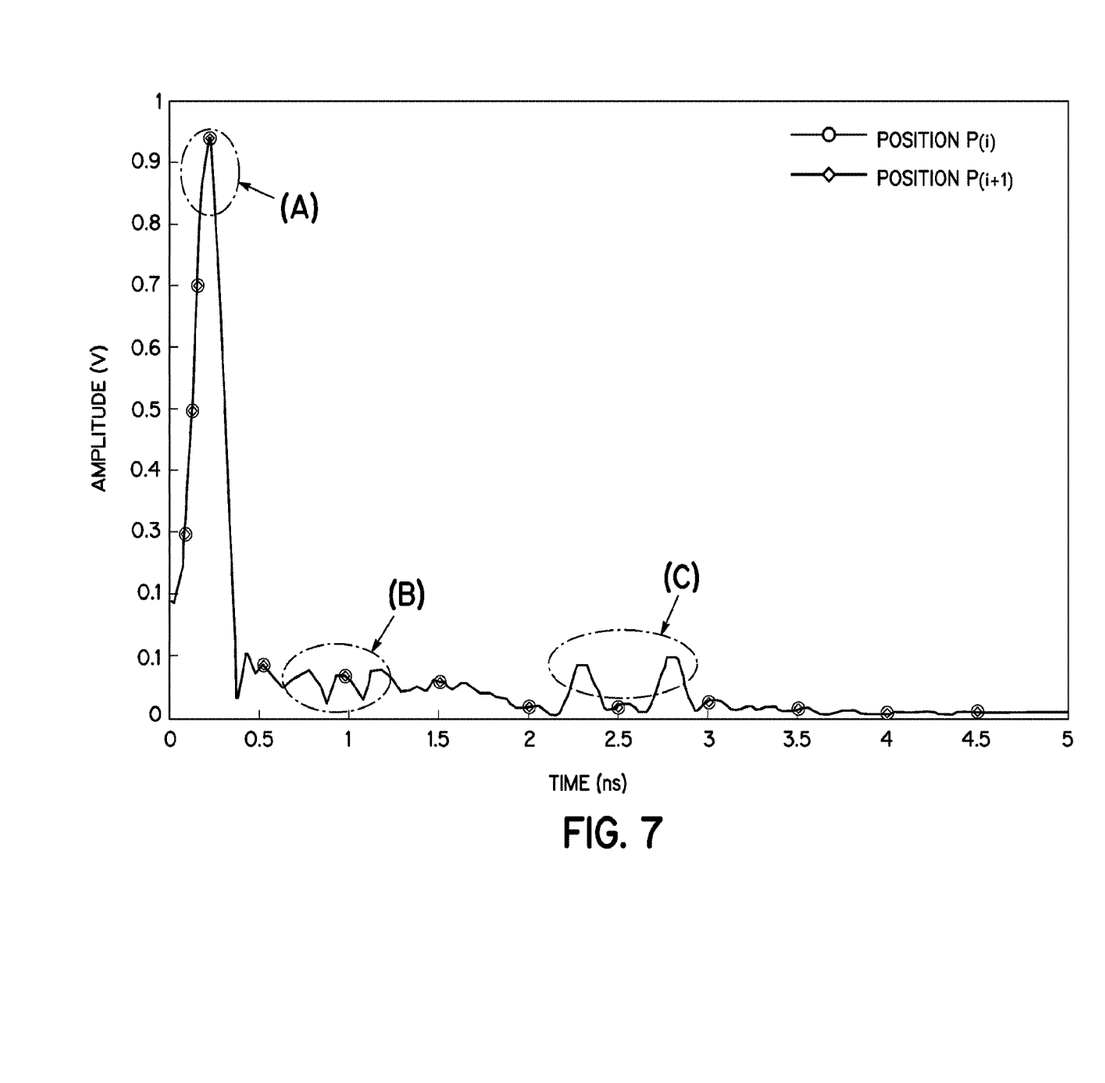
FIG. 7 is a graphical illustration of the acquired signals from two adjacent positions.

Examples of $S^i(t)$ and $S^{i+1}(t)$ acquired at $P_i$ and $P_j$ are shown in FIG. 7. The signals at the first and second positions include at least three regions of interest, including: (A) combination of $S_{coupling}^i(t)$ and $S_{skin}^i(t)$; (B) $S_{target}^i(t)$, which is immersed within the noise and other scattered signals; and (C) $S_{mr}^i(t)$. The signal attributed to reflection at the tumor/glandular tissue interface has an intensity that is substantially equal to the noise signals within the same region of interest. Thus, isolation of $S_{target}^i(t)$ within the total acquired signal is difficult.

To extract the target signal, $S_{target}^i(t)$ in accordance with one embodiment of the present invention, the signals measured from the first and second positions, $S^i(t)$, $S^{i+1}(t)$, are then calibrated. As an available choice, the frequency response of the coupling between the Tx and Rx antennae 22, 24 may also be measured in an antenna chamber (not shown) and used to separate the skin reflections, $S_{skin}^i(t)$. In that regard, a tissue boundary in each acquired signal is determined (Block 102).

Figure 12:
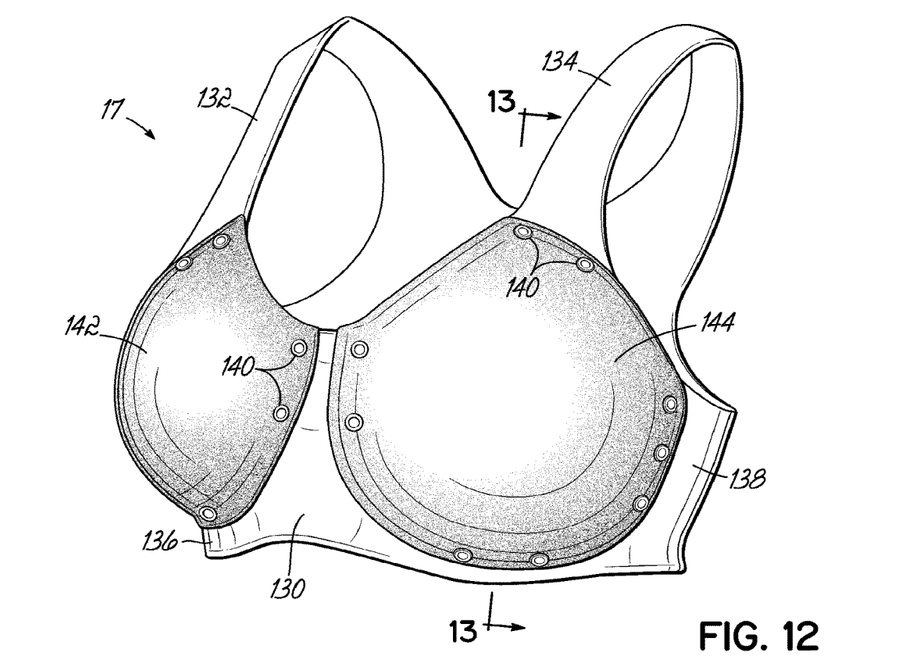
FIG. 12 is perspective view of a microwave imaging system incorporated into a brassiere for detection of breast cancer in accordance with another embodiment of the present invention.
Figure 13:
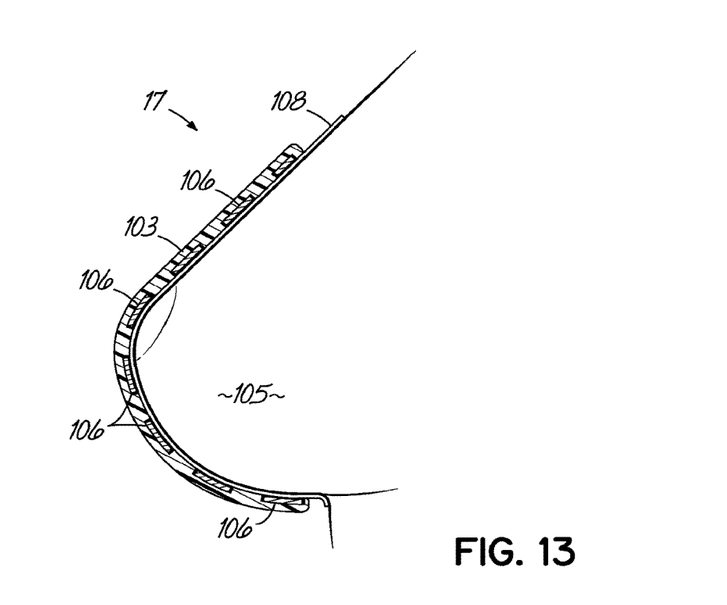
FIG. 13 is a cross-sectional view of the brassiere of FIG. 12, taken along the line 13-13 in FIG. 12.

In some embodiments, such as is shown in FIG. 13, a polymeric liner 103 may be used to match the impedance with the breast 105 and to eliminate air at the skin boundary of the breast 105 for optimal signal propagation across the skin boundary. The polymeric liner 103 also simplifies computational modeling of the received signals. The polymeric liner 103 may be flexible and constructed from a polymer material having suitable dielectric properties for transmission of the microwave signals. The polymer material may be disposable, such as after a single use/patient. In still other embodiments, such as is shown in FIG. 13, the transducers 106 may be encapsulated within the polymer material comprising the polymeric liner, and wherein an additional liner 108 may be used for hygienic purposes. The additional liner 108 may also include the fabric of the brassiere 17 (FIG. 12), which may, itself, be washable or disposable. Use of the polymeric liner 103 may reduce and/or eliminate the need for matching gels; however, use of such matching gels is not precluded. Furthermore, though not specifically shown, the polymeric liner 103 may be incorporated into other embodiments of the present invention, including, for example, the imaging cups 14, 16 of FIG. 1.

With the tissue boundary identified, the signal acquired at each position is corrected with the signal acquired at an adjacent position. More specifically, the signal acquired at the first position, $P_i$, is corrected by subtracting the signal acquired at the second position, $P_{i+1}$ (Block 104). The corrected signal, $S_{corrected}(t)$, is generally described as a midpoint between the first and second positions and is given by:

$$S_{corrected}(t) = S^{i+1}(t) - S^i(t)$$

Figure 8:
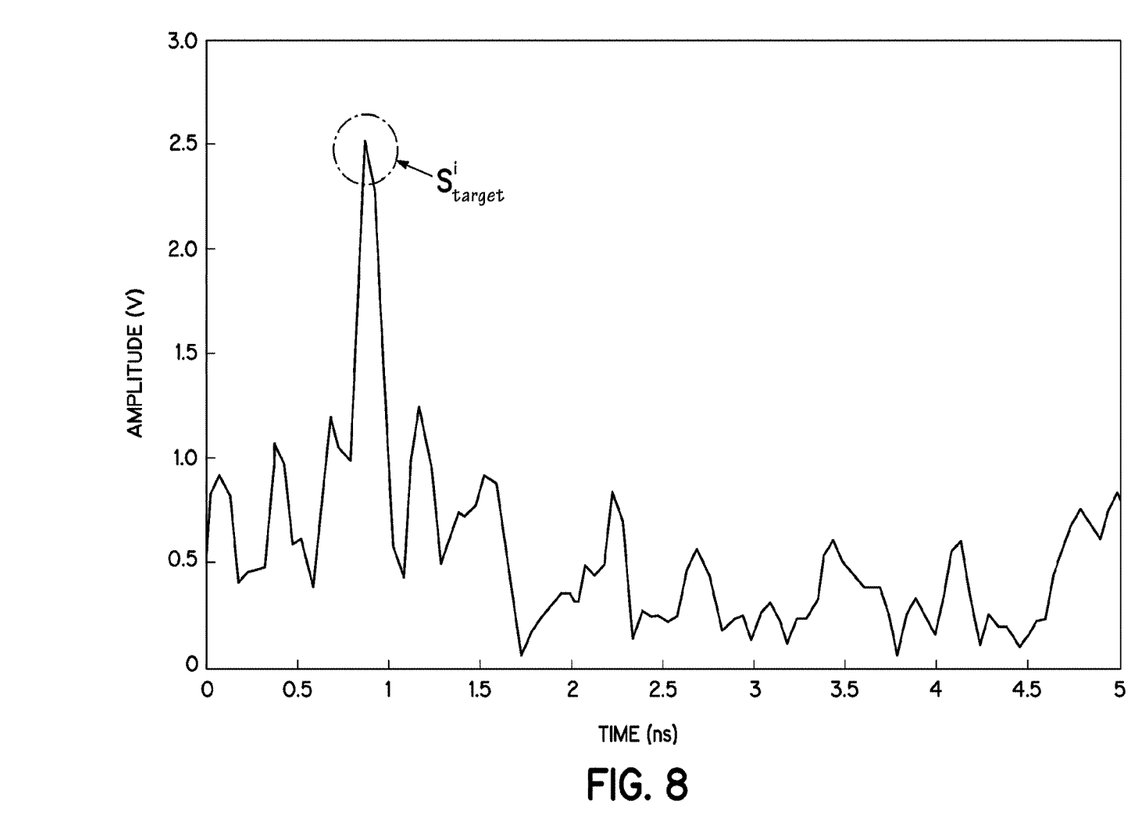
FIG. 8 is a graphical illustration of the processed signal from the two acquired signal of FIG. 7.

One example of a corrected signal shown in FIG. 8. Since the positions of Tx and Rx antennae 22, 24 (FIG. 2) are fixed, the signal due to coupling, $S_{coupling}^i(t)$, is constant and cancelled in the calibration process. The signal due to backscatter from the skin interface, $S_{skin}^i(t)$, are largely eliminated via calibration as well. Finally, signals due to multi-reflections, $S_{mr}^i(t)$, have a longer time delay and may be gated in the time domain.

With $S_{corrected}(t)$ calculated, the signal due to the target, $S_{target}^i(t)$, is readily identifiable as compared with the surrounding noise. Said another way, the signal-to-noise ratio between the signal due to the target, $S_{target}^i(t)$, is significantly greater in $S_{corrected}(t)$ as compared to $S^i(t)$ or $S^{i+1}(t)$.

Returning again to FIG. 6, with the corrected signal calculated, an image may be reconstructed from the each $S_{corrected}^{(i+1)-i}(t)$ (Block 106). While image reconstruction may include various algorithms and computational methods, one suitable image reconstruction may be, for example, a three-dimensional beamformer used to recover the target image. More specifically, one suitable beamformer is provided in detail in Y. WANG et al. "Three-Dimensional Through Wall Imaging Using an UWB SAR," *IEEE AP-S Int. Symp. On Anteannas and Propagat.* Toronto, CA (July 2010). Briefly, the imaged breast may be divided into cubic voxels in x-, y-, and z-planes. For a given voxel, V(x, y, z), a delay and sum ("DAS") algorithm is applied to calculate image information. The DAS algorithm is given by:

$$S(x, y, z) = \sum_{m=1}^{M} \sum_{n=1}^{N} w_{m,n}(x, y, z) s_{m,n} e^{j\varphi_{m,n}(x,y,z)}$$

Where $s_{m,n}$ is the signal received by the Rx antenna at $P_i$ ("m") and $P_{i+1}$ ("n"), $w_{m,n}(x, y, z)$ introduces the magnitude compensation for different scattering loss and propagation loss, and $\varphi_{m,n}(x, y, z)$ introduces the phase compensation for different phase delays. The DAS algorithm is applied to each $S_{corrected}^{(i+1)-i}(t)$ and the completed three-dimensional image is displayed, one example of which is shown in FIG. 9.

Figure 9:
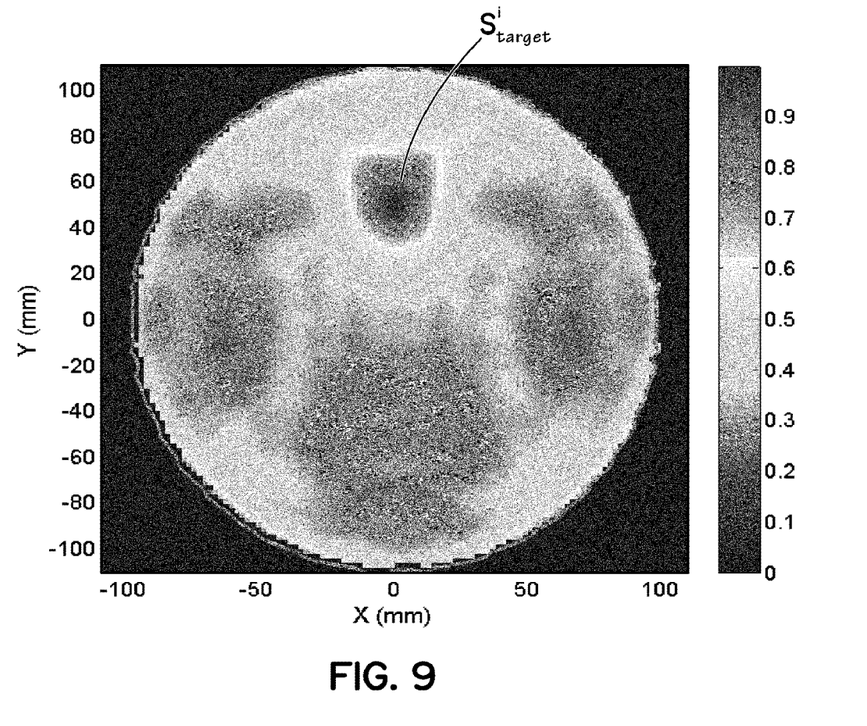
FIG. 9 is an exemplary image reconstructed from acquired signals in accordance with an embodiment of the present invention.

Referring specifically to the reconstructed image of FIG. 9, the region indicated by the high intensity, normalized signal, e.g., $S_{target}^{i}(t)$ is associated with the target or tumor.

Figure 10:
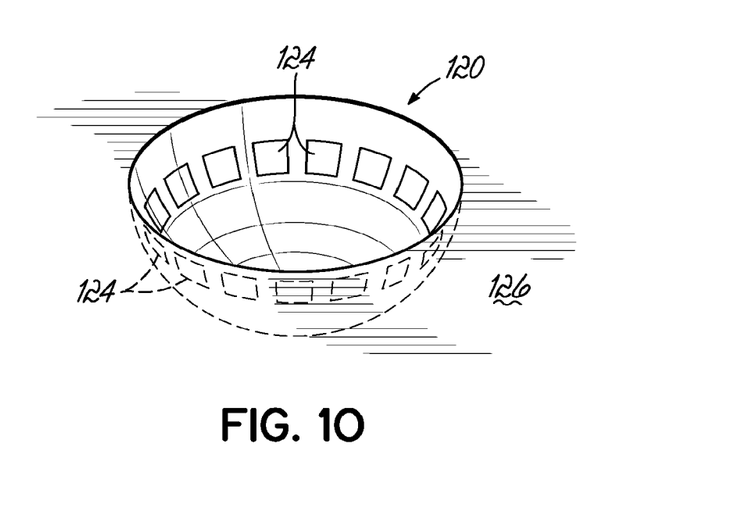
FIG. 10 is an imaging cup in accordance with another embodiment of the present invention.
Figure 11:
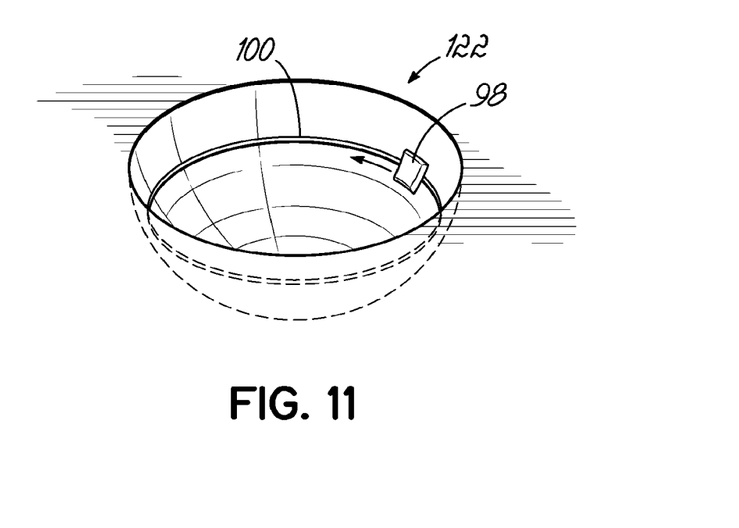
FIG. 11 is an imaging cup in accordance with still another embodiment of the present invention.

Turning now to FIGS. 10 and 11, imaging cups 120, 122 in accordance with additional embodiments of the present invention are shown and described. In particular, in FIG. 10, the transducers 124 are positioned circumferentially about the imaging cup along a single plane 126 through the imaging cup 120. The transducers 124 may be arranged in any type of configuration around the imaging cup 120. The particular embodiment of the imaging cup 120 reduces the number of signals "n," to be acquired and the number of corrected signals, $S_{target}^{i}(t)$, to be calculated, thus reducing manufacturing costs, image construction time, and computer hardware and software capabilities.

In FIG. 11, still another imaging cup 122 and comprises the single transducer 98 and the track 100. A motor (not shown) is configured to move the transducer 98, by a discrete distance, along the track 100 for acquiring the signals, $S^{i+1}(t)$, from the "n" positions. While the particular embodiment includes only one transducer 98 and significantly reduces the amount of antenna-coupling from adjacent transducers 18 (FIG. 1), movement of the individual transducer 98 along the track 100 may increase the procedure time required for imaging one breast. In still other embodiments, multiple transducers may be operably coupled to the track 100, or alternatively, associated with separate tracks within the imaging cup.

Turning now to FIG. 12, the brassiere 17 for use with the imaging system in accordance with one embodiment of the present invention is described in greater detail. The brassiere may be constructed, as noted above, from a washable or disposable material and includes a chest portion 130, shoulder straps 132, 134, and chest straps 136, 138. The chest portion 130 may be sized and shaped with cups for receiving the left and right breasts, as indicated above. Accordingly, various brassiere sizes may be manufactured and correspond to conventional brassiere sizing.

The chest portion 130 may further include one or more coupling devices 140 that are configured to operably couple one or two imaging cups 142, 144 to the chest portion 130. Each of the imaging cups 142, 144 may be constructed from material similar to the polymeric liner 103 (FIG. 13) described above, which may include an outer covering material if desired. Accordingly, the imaging cups 142, 144 would be coupled to the brassiere 17 via the one or more coupling devices 140 during the signal acquisition protocol. Yet, it would be readily understood that the polymeric liner material need not be required.

Figure 14:
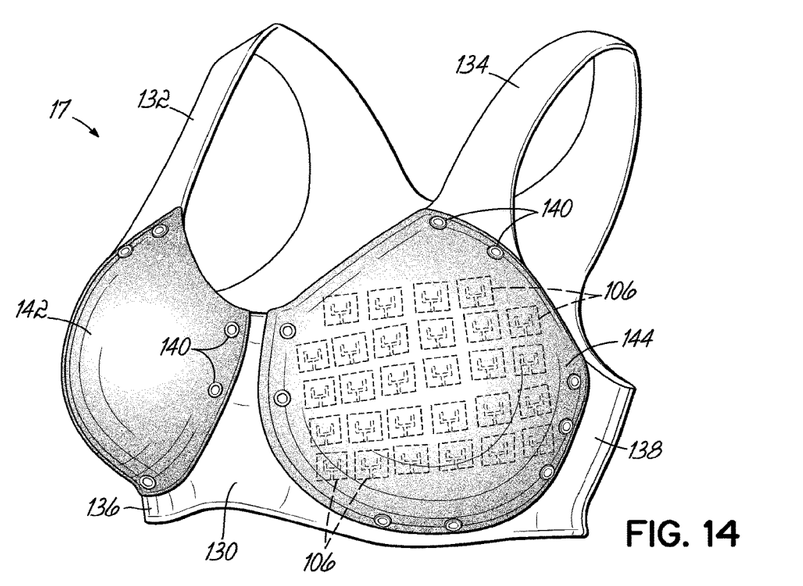
FIG. 14 is a perspective view of a microwave imaging system incorporated into a brassiere for detection of breast cancer in accordance with still another embodiment of the present invention.
Figure 15:
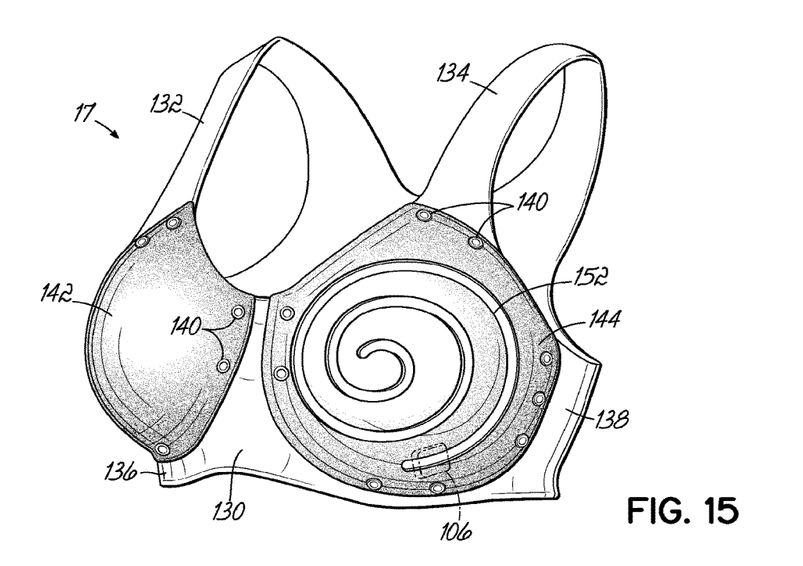
FIG. 15 is a perspective view of a microwave imaging system incorporated into a brassiere for detection of breast cancer in accordance with another embodiment of the present invention.

In FIG. 14, the imaging cups 142, 144 are shown with the plurality of transducers 106 shown in phantom. As was described above, the plurality of transducers 106 may be arranged in one or more rows with each adjacent transducer being separated by a small distance or angle. Alternatively, and as shown in FIG. 15, the brassiere 17 in accordance with another embodiment is shown wherein the imaging cup 142, 144 includes a track 152 that is similar to the track 100 (FIG. 11) described above. The track may be radial, as was shown in FIG. 11, or may be spiral in shape to cover the entire area of the breast for imaging by a single transducer or a transducer array.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. For example, it will be appreciated that a tissue support or imaging cup may have different geometries depending upon the tissue to be imaged. Thus, while the term "cup" is used herein in connection with imaging breast tissue, it will be appreciated that an imaging cup consistent with the invention need not necessarily have a cup-like shape. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A medical imaging device comprising:
   a tissue support having a size and shape to receive a tissue;
   a plurality of transducers operably coupled to the tissue support, each of the plurality of transducers having a transmitting antenna and a receiving antenna, the transmitting antenna operable in a frequency range of 2 GHz to 8 GHz and the receiving antenna operable in a frequency range of 2 GHz to 8 GHz, wherein a select one of the plurality of transducers transmits a first signal and receives a first total signal and an adjacent one of the plurality of transducers transmits a second signal and receives a second total signal;
   a controller configured to calculate a calibrated signal by subtracting the second total signal from the first total signal.

2. The medical imaging device of claim 1, wherein each of the plurality of transducers is radially-spaced away from an adjacent one of the plurality of transducers by an angle that ranges from 0.5 degrees to 5 degrees.

3. The medical imaging device of claim 1, wherein each of the plurality of transducers is linearly-spaced away from an adjacent one of the plurality of transducers by a distance that ranges from 1 mm to 20 mm.

4. The medical imaging device of claim 1, wherein the controller is further configured to construct an image of the tissue from the calibrated signal.

5. The medical imaging device of claim 1, wherein the tissue support is a breast imaging cup.

6. The medical imaging device of claim 5, wherein the breast imaging cup is operably coupled to a brassiere.

7. The medical imaging device of claim 1, wherein the medical imaging device is part of an imaging system that includes a support configured to support the at least one medical imaging device in an anatomical arrangement suitable for imaging a tissue of a patient.

8. The medical imaging device of claim 7, wherein the imaging system further includes:
   a second tissue support having a size and shape to receive a tissue;

a second plurality of transducers operably coupled to the second tissue support, each of the second plurality of transducers having a transmitting antenna and a receiving antenna, the transmitting antenna operable in a frequency range of 2 GHz to 8 GHz and the receiving antenna operable in a frequency range of 2 GHz to 8 GHz, wherein a select one of the second plurality of transducers transmits a third signal and receives a third total signal and an adjacent one of the second plurality of transducers transmits a fourth signal and receives a fourth total signal, and each of the tissue supports is a breast imaging cup, one of the tissue cups being configured to receive a left breast and the tissue cup being configured to receive a right breast.

9. The medical imaging device of claim 1 wherein the transmitting antenna and the receiving antenna are the same antenna.

10. The medical imaging device of claim 1 further comprising an alternating signal generator communicatively coupled to the plurality of transducers.

11. The medical imaging device of claim 1 further comprising a voltage control oscillator communicatively coupled to the plurality of transducers.

12. The medical imaging device of claim 1 further comprising a signal amplifier communicatively coupled to the plurality of transducers.

13. The medical imaging device of claim 1 further comprising a track operably coupled to the tissue support, the plurality of transducers moveable along the track between a first position and a second position.

* * * * *